US010844397B2

(12) United States Patent
Schmidt

(10) Patent No.: US 10,844,397 B2
(45) Date of Patent: Nov. 24, 2020

(54) **TRANSGENIC PLANT SPECIES ENGINEERED TO INHIBIT BIOSYNTHESIS OF *ASPERGILLUS* AFLATOXIN**

(71) Applicant: ARIZONA BOARD OF REGENTS ON BEHALF OF THE UNIVERSITY OF ARIZONA, Tucson, AZ (US)

(72) Inventor: Monica Schmidt, Tucson, AZ (US)

(73) Assignee: ARIZONA BOARD OF REGENTS ON BEHALF OF THE UNIVERSITY OF ARIZONA, Tucson, AZ (US)

( * ) Notice: Subject to any disclaimer, the term of this patent is extended or adjusted under 35 U.S.C. 154(b) by 269 days.

(21) Appl. No.: 15/579,167

(22) PCT Filed: Jun. 1, 2016

(86) PCT No.: PCT/US2016/035300
§ 371 (c)(1),
(2) Date: Dec. 1, 2017

(87) PCT Pub. No.: WO2016/196654
PCT Pub. Date: Dec. 8, 2016

(65) Prior Publication Data
US 2018/0355371 A1  Dec. 13, 2018

Related U.S. Application Data

(60) Provisional application No. 62/169,153, filed on Jun. 1, 2015.

(51) Int. Cl.
*C12N 15/82* (2006.01)
*C12N 9/10* (2006.01)

(52) U.S. Cl.
CPC ....... *C12N 15/8282* (2013.01); *C12N 9/1029* (2013.01); *C12N 15/8218* (2013.01); *C12Y 203/01* (2013.01)

(58) Field of Classification Search
None
See application file for complete search history.

(56) References Cited

U.S. PATENT DOCUMENTS

| | | | |
|---|---|---|---|
| 4,945,050 A | 7/1990 | Sanford et al. | |
| 5,036,006 A | 7/1991 | Sanford et al. | |
| 5,100,792 A | 3/1992 | Sanford et al. | |
| 5,942,661 A | 8/1999 | Keller | |
| 8,436,162 B2 * | 5/2013 | Brown | C07K 14/415 435/419 |
| 8,772,254 B2 * | 7/2014 | Bogaert | C12N 15/111 514/44 A |
| 2003/0188344 A1 | 10/2003 | Lynn et al. | |
| 2005/0026290 A1 | 2/2005 | Ciardi et al. | |
| 2005/0118690 A1 * | 6/2005 | Roberts | C07K 14/38 435/135 |
| 2006/0160223 A1 | 7/2006 | Lacour et al. | |
| 2008/0152641 A1 | 6/2008 | Haas et al. | |

FOREIGN PATENT DOCUMENTS

WO   WO2014013074 A1   1/2014

OTHER PUBLICATIONS

Feng et al (J. Bacteriol., 1995, 177(21): 6246-6254).*
Alakonya et al (2013, Aflatoxins—Recent Advances and Future Prospects, Chapter 3: A New Approach in Aflatoxin Management in Africa: Targeting Aflatoxin/Sterigmatocystin Biosynthesis in *Aspergillus* Species by RNA Silencing Technique, IntechOpen, Mehdi Razzaghi-Abyaneh).*
Wang et al (BMC Biotechnol., 2006, 6: 50).*
GenBank AAC41675.1 (published online 1995).*
Moore. GG et al. Recombination and Lineage-Specific Gene Loss in The Aflatoxin Gene 2. 19 Cluster of Aspergillus Flavus. Molecular Ecology. Dec. 2009. vol. 18. No. 23; pp. 4870-4887; abstract; p. 4870. column 1, paragraph 1; p. 4871, col. 1. paragraph 3; 001: 10.1111/j.1365-294X.2009.04414.
Chang. PK et al. Understanding Nonaflatoxigenicity of Aspergillus sojae: a Windfall of 5 Aflatoxin Biosynthesis Research. Applied Microbiology and Biotechnology. Jul. 31, 2007, vol. 76, No. 5; pp. 977-984; Genbank supplement 1-3; 001: 10.1007/s00253-007-1116-4.
Atehnkeng et al., 2008 Food Additives and Contaminants, Part A 25:1264.
Bass, Double-Stranded RNA as a Template for Gene Silencing, Cell, vol. 101, Issue 3, Apr. 28, 2000, pp. 235-238.
Bosher and Labouesse, RNA interference: genetic wand and genetic watchdog, Nature Cell Biology 2, E31-E36 (2000).
Catalanotto et al., Transcription: Gene silencing in worms and fungi, Nature, 404, 245, (2000).
Cogoni and Macino, Post-transcriptional gene silencing across kingdoms. Current Opinion in Genetics & Development. vol. 10, Issue 6, Dec. 1, 2000, pp. 638-643.
Dalmay et al., An RNA-Dependent RNA Polymerase Gene in *Arabidopsis* Is Required for Posttranscriptional Gene Silencing Mediated by a Transgene but Not by a Virus. Cell, vol. 101, Issue 5, May 26, 2000, pp. 543-551.
Dernburg et al., Transgene-mediated cosuppression in the C. elegans germ line, Genes & Dev. 2000. 14:1578-1583.
Dhiraj Thakare, Jianwei Zhang , Rod A. Wing, Peter J. Cotty and Monica A. Schmidt, Aflatoxin-free transgenic maize using host-induced gene silencing. Science Advances Mar. 10, 2017: vol. 3, No. 3, e1602382 DOI: 10.1126/sciadv.1602382.

(Continued)

*Primary Examiner* — Stephen Uyeno
(74) *Attorney, Agent, or Firm* — Nguyen Tarbet

(57) ABSTRACT

Transgenic plant species engineered to inhibit aflatoxin production in *Aspergillus* species, methods of producing such transgenic plant species that can inhibit aflatoxin production, and compositions for such transgenic plant production. The transgenic plants harbor an RNAi cassette expressing dsRNA for an enzyme, such as aflC, that is required for aflatoxin biosynthesis. The dsRNA may include at least one, at least two, at least three, or more than three sections of the target enzyme gene.

Figure 1A:
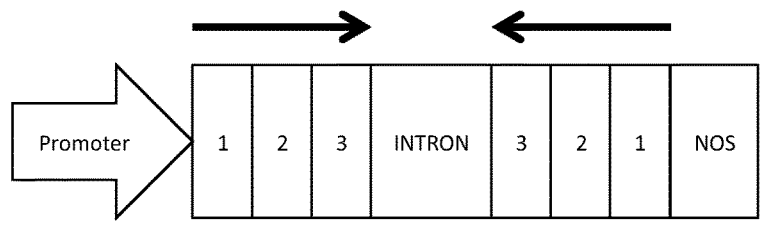
Figure 1B:
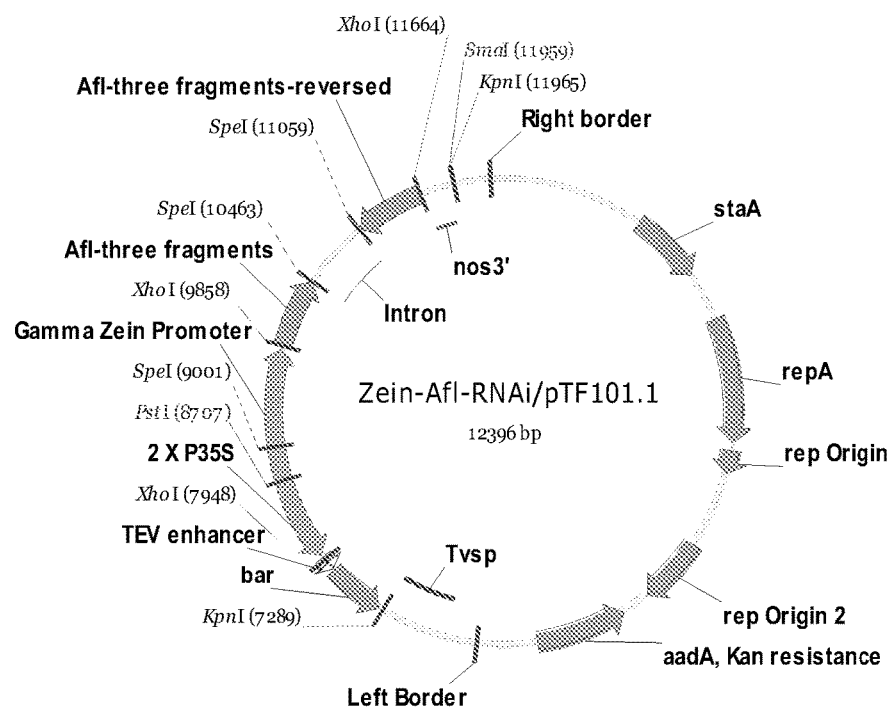
Figure 1C:
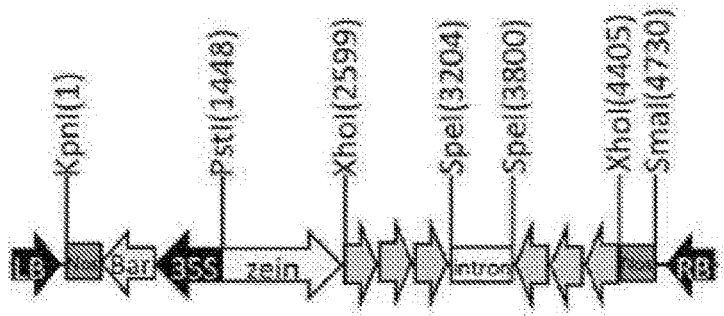

9 Claims, 2 Drawing Sheets
Specification includes a Sequence Listing.

(56) References Cited

OTHER PUBLICATIONS

Fire et al., Potent and specific genetic interference by double-stranded RNA in Caenorhabditis elegans. Nature, 391, 306-811 (Feb. 19, 1998).
Fire, A., RNA-triggered gene silencing. Trends in Genetics. vol. 15, Issue 9, Sep. 1, 1999, pp. 358-363.
Hamilton and Baulcombe, A Species of Small Antisense RNA in Posttranscriptional Gene Silencing in Plants, Science Oct. 29, 1999:vol. 286, Issue 5441, pp. 950-952.
Hofgen & Willmitzer (1988) Nucleic Acids Res. 16:9877.
Ketting and Plasterk, Current Opinion in Genetics & Development, vol. 10, Issue 5, Oct. 1, 2000, pp. 562-567.
Miki et al. "Procedures for Introducing Foreign DNA into Plants" in Methods in Plant Molecular Biology and Biotechnology, Glid, B. R. and Thompson, J. E. Eds. CRC Press, Inc., Boca Raton, 1993, pp. 67-88.
Mourrain et al., *Arabidopsis* SGS2 and SGS3 Genes Are Required for Posttranscriptional Gene Silencing and Natural Virus Resistance. Cell, vol. 101, Issue 5, May 26, 2000, pp. 533-542.
Pelissier, A DNA target of 30 bp is sufficient for RNA-directed DNA methylation, RNA, vol. 6, Issue Jan. 1, 2000, pp. 55-65.
Wassenegger, RNA-directed DNA methylation, Plant Molecular Biology, Jun. 2000, vol. 43, Issue 2-3, pp. 203-220.
Rakowoczy-Trojanowska Cell. Mol. Biol. Lett. 7:849-858 (2002).
Sharp, RNA Interference, Science Mar. 31, 2000: vol. 287, Issue 5462, pp. 2431-2433.
Sijen and Kooter, Post-transcriptional gene-silencing: RNAs on the attack or on the defense? BioEssays, vol. 22, Issue 6 Jun. 2000 pp. 520-531.
Smardon et al., EGO-1 is related to Rna-directed RNA polymerase and functions in germ-line development and RNA interference in C. elegans, Cell Biology. vol. 10, Issue 4, Feb. 15, 2000, pp. 169-178.
Uknes et al. (1993) Plant Cell 5:159-169.
Yu et al., 2004, Appl Environ Microbiol 70(3):1253-1262.
Zamore et al., RNAi: Double-Stranded RNA Directs the ATP-Dependent Cleavage of mRNA at 21 to 23 Nucleotide Intervals, Cell, vol. 101, Issue 1, 31 Mar. 2000, pp. 25-33.

\* cited by examiner

TRANSGENIC PLANT SPECIES ENGINEERED TO INHIBIT BIOSYNTHESIS OF *ASPERGILLUS* AFLATOXIN

CROSS REFERENCE

This application claims priority to U.S. Provisional Patent Application No. 62/169,153, filed Jun. 1, 2015, the specification(s) of which is/are incorporated herein in their entirety by reference.

FIELD OF THE INVENTION

The present invention relates to aflatoxins, which are secondary metabolites produced by certain species of *Aspergillus* (e.g., *A. flavus, A. parasiticus*), more particularly to transgenic plant species, such as maize and peanuts, that express RNAi against a gene required for the biosynthesis of aflatoxin.

BACKGROUND OF THE INVENTION

Aflatoxin is a toxic secondary compound produced by a fungal source and can be responsible for massive agricultural losses worldwide. It is estimated that 25% of the world's crops are contaminated with some sort of mycotoxin, aflatoxin being chief among them. Worldwide there is a net loss of 16 million tons of maize due to aflatoxin contamination. Aflatoxin contamination in crops, and subsequently livestock, threatens greater agricultural development, food security and human health. The fungus *Aspergillus* produces aflatoxins that are toxic and carcinogenic to livestock animals and humans. When aflatoxin-contaminated food/feed is ingested it can result in hepatotoxicity, liver cancer, kwashiorkor and Reye's syndrome. Due to its high toxicity over 100 countries restrict the level of aflatoxin in food and feed. The US Department of Agriculture regulates the allowable level of aflatoxin in maize for livestock feed and human consumption. Maize destined for human food and dairy cattle feed has the tightest limit of 20 parts per billion (ppb). To put this number into perspective, 1 ppb is equivalent to a single drop of water in a 21,700 gallon (82,135 liter) swimming pool or from a time perspective, 1 sec in 31.7 yrs.

The present invention features transgenic plant species engineered to inhibit the biosynthesis of *Aspergillus* aflatoxin, methods of producing said transgenic plant species, and compositions used for the production of said transgenic plant species. The transgenic plant species express RNAi against an *Aspergillus* gene required for the biosynthesis of aflatoxin. For example, the present invention features transgenic maize (or peanut plants) comprising a cassette engineered to express RNAi against a gene (e.g., aflC) required for *Aspergillus* aflatoxin biosynthesis. Inventors have produced nine transgenic lines of maize (cultivar B73 hybrid) by *Agrobacterium*-mediated transformation and have confirmed by molecular means the insertion of both the bar selectable marker gene, conferring the added bialaphos herbicide resistance trait, and the RNAi aflatoxin suppression cassette. To date, two lines have been bred to homozygosity. Results from preliminary on-plant cob *Aspergillus* infections, with subsequent toxin quantification, indicates this RNAi strategy is effective to reduce aflatoxin by at least 80% in developing transgenic maize kernels.

The strategies may be effective to suppress aflatoxin in any appropriate affected crop system (e.g., the promoter used in the RNAi construct/cassette may be changed to express in the target tissue of the target crop). The present invention is not limited to maize and peanut plants. For example, in some embodiments, the plant is cotton, cobra, soybean, sorghum, millet, rice, etc.

SUMMARY OF THE INVENTION

The present invention features transgenic plant species engineered to inhibit the biosynthesis of *Aspergillus* aflatoxin, methods of producing said transgenic plant species, and compositions used for the production of said transgenic plant species. For example, the present invention features a transgenic plant species (e.g., maize species, peanut species, etc.) engineered to inhibit biosynthesis of *Aspergillus* aflatoxin, e.g., to inhibit biosynthesis of a polyketide synthase (e.g., aflC). The major aflatoxins that contaminate agricultural commodities, e.g., B1 ($AFB_1$), B2 ($AFB_2$), G1 ($AFG_1$), and G2 ($AFG_2$), and their chemical structures, are known to one of ordinary skill in the art. A detailed exemplary biosynthetic pathway can be found in Yu et al., 2004, Appl Environ Microbiol 70(3):1253-1262).

The present invention features an RNAi cassette, wherein the cassette comprises a dsRNA template and a selectable marker (e.g., bialaphos resistance (bar) gene) under control of a plant-specific promoter (e.g., endosperm, glycinin, etc.). The dsRNA template comprises a sequence for at least one section (at least two sections, at least three sections, more than three sections, etc.) of a gene encoding an enzyme (e.g., aflC) required for *Aspergillus* aflatoxin biosynthesis. The present invention is not limited to the aforementioned promoters or selectable markers. The present invention is not limited to maize and peanut plants.

In some embodiments, one or more of the sections of the gene (encoding the enzyme, e.g., aflC) used in the cassette are from 50 to 400 bp in length. In some embodiments, one or more of the sections of the gene are from 100 to 300 bp in length. In some embodiments, one or more of the sections of the gene are from 150 to 250 bp in length (e.g., from 190-210 bp, e.g., 200 bp, etc.). In some embodiments, the sequence for targeting a section of the gene is at least 90% homologous to its target sequence. In some embodiments, the sequence for targeting a section of the gene is at least 95% homologous to its target sequence. In some embodiments, the sequence for targeting a section of the gene is at least 99% homologous to its target sequence. In some embodiments, the sequence for targeting a section of the gene is at least 90% homologous to its target sequence. In some embodiments, the sequence for targeting a section of the gene is at least 95% homologous to its target sequence. In some embodiments, the sequence for targeting a section of the gene is at least 99% homologous to its target sequence. In some embodiments, the RNAi cassette is within a host (e.g., *Agrobacterium*).

The present invention also features an RNAi complex comprising at least a section of an mRNA of an enzyme required for *Aspergillus* aflatoxin biosynthesis (e.g., aflC), e.g., a target mRNA sequence of the enzyme; and a siRNA directed to the target mRNA sequence of the mRNA for the enzyme required for *Aspergillus* aflatoxin biosynthesis (e.g., aflC), wherein the siRNA is hybridized to the target mRNA sequence. In some embodiments, the enzyme required for *Aspergillus* aflatoxin biosynthesis is aflC. In some embodiments, the siRNA is from 20 to 25 bp in length. In some embodiments, the siRNA is at least 90% homologous to its target mRNA sequence. In some embodiments, the siRNA is at least 99% homologous to its target mRNA sequence.

The present invention also features an RNAi complex comprising RISC and a siRNA directed to a target mRNA sequence of an mRNA for an enzyme required for *Aspergillus* aflatoxin biosynthesis. In some embodiments, the enzyme required for *Aspergillus* aflatoxin biosynthesis is aflC. In some embodiments, the siRNA is from 20 to 25 bp in length. In some embodiments, the siRNA is at least 90% homologous to its target mRNA sequence. In some embodiments, the siRNA is at least 99% homologous to its target mRNA sequence.

The present invention also features a method of producing a transgenic plant species. For example, in some embodiments, the method comprises introducing to a plant species an RNAi cassette according to the present invention. The RNAi cassette may be within a host (e.g., *Agrobacterium*), wherein the host is capable of introducing the RNAi cassette into the plant species (e.g., via infection).

In some embodiments, the method comprises introducing to a host an RNAi cassette according to the present invention, and transferring the RNAi cassette from the host to a plant species. In some embodiments, the RNAi cassette is introduced into the host via electroporation. The present invention is not limited to these methods. For example, in some embodiments, transgenic plants can also be produced by particle bombardment (e.g., biolistics).

The present invention also features an RNAi cassette comprising a dsRNA template and a selectable marker both operatively linked to a plant-specific promoter, wherein the dsRNA template encodes at least two sections (e.g., two, at least three, three, more than three, etc.) of a gene of a polyketide synthase of *Aspergillus* aflatoxin biosynthesis (e.g., alfC), wherein the dsRNA template is adapted to produce RNAi to inhibit synthesis of the polyketide synthase of *Aspergillus* aflatoxin biosynthesis. In some embodiments, the dsRNA template comprises SEQ ID NO: 2. In some embodiments, the sections of the gene of the polyketide synthase span at least 75% of a length of the gene of the polyketide synthase, at least 90% a length of the gene of the polyketide synthase, at least 95% of the gene, etc. In some embodiments, the sections of the gene of the polyketide synthase are from 100 to 300 bp in length. In some embodiments, the plant-specific promoter comprises an endosperm promoter or a glycinin promoter. In some embodiments, the selectable marker comprises a bialaphos resistance (bar) gene. In some embodiments, the cassette is within a host, e.g., *Agrobacterium*.

The present invention also features a transgenic plant (e.g., maize, peanut, etc.) engineered to inhibit synthesis of *Aspergillus* aflatoxin, wherein the transgenic plant expresses an RNAi cassette according to the present invention. The dsRNA template is expressed in the transgenic plant thereby producing RNAi adapted to inhibit synthesis of the polyketide synthase. The present invention also features a kit comprising an RNAi cassette according to the present invention. The present invention also features a host (e.g., *Agrobacterium*) comprising an RNAi cassette according to the present invention. The present invention also features a method of producing a transgenic plant engineered to inhibit synthesis of *Aspergillus* aflatoxin. In some embodiments, the method comprises introducing to a plant a host comprising an RNAi cassette according to the present invention, wherein said host introduces the RNAi cassette into the plant, wherein the RNAi cassette is expressed in the plant thereby producing RNAi adapted to inhibit synthesis of the polyketide synthase of *Aspergillus* aflatoxin biosynthesis.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

FIG. 1A shows an example of an RNAi cassette to target suppression of the *Aspergillus* polyketide synthase [aflC (pksA), 2109 amino acids] gene by targeting three sections simultaneously in a single cassette. The function of the polyketide synthase is imperative to the production of aflatoxins. Since the aflC gene is over 7 kb in length, a single RNAi cassette was formed that targets three segments of the gene in areas that have displayed no homology to the host plants or downstream consumers. In some embodiments, the sequence of the target gene is placed in inverted tandem repeats to produce a hairpin RNA. The RNAi cassette shown in FIG. 1A was placed under a promoter, e.g., the endosperm specific promoter for maize transformation, the glycinin seed specific promoter for peanut transformation, etc. Note: 1=section 1, 2=section 2, 3=section 3). In some embodiments, section 1 is a 5' region of the gene, e.g., aflC gene. In some embodiments, section 2 is a middle region of the gene, e.g., aflC gene. In some embodiments, section 3 is a 3' region of the gene, e.g., aflC gene. In some embodiments, the cassette comprises 1 section. In some embodiments, the cassette comprises 2 sections. In some embodiments, the cassette comprises 3 sections. In some embodiments, the cassette comprises more than 3 sections.

FIG. 1B and FIG. 1C show additional examples of RNAi cassettes. The present invention is not limited to the cassettes of FIG. 1B and FIG. 1C.

FIG. 2 shows preliminary aflatoxin assays on RNAi aflC transgenic maize kernels from line #5 (RNAi aflC line #5, homozygous), line #20 (RNAi aflC #20, heterozygous), and nontransgenic control (B73 cultivar). Kernels deemed highly infected and medium-low infected with *Aspergillus* were subjected to aflatoxin TLC analysis. The graphs show aflatoxin levels detected in ppb. Both RNAi aflC lines show much reduced levels of aflatoxin (80% in high infected kernels and nondetectable levels in medium-low infection kernels).

FIG. 3 shows RT-PCR analysis of total RNA isolated from developing kernels. cDNA produced from RNA isolated from 2 plants of 3 transgenic RNAiAFL lines (4, 5, 20) and a null plant were used to amplify a 169 bp segment of the inserted RNAiAFL cassette (top) and amplify a 280 bp endogenous maize gene (GAP; glyceraldehyde 3 phosphate dehydrogenase)(lanes 1-7 cDNA from transgenics; lane 8 genomic DNA from AFLline 4a). The presence of the RNAi cassette amplicon indicates its expression in the lines tested and not in the null control. Control amplification indicates cDNA was amplified in transgenic cDNA samples, not genomic DNA as indicated by the amplicon size difference.

FIG. 4 shows a graphical representation of log 2 ppb toxin levels detected in tested transgenic RNAiAFL lines (see Example 2) with ANOVA with post-hoc Tukey HSD performed at 95% confidence levels statistical analysis. Means displaying different letters are significantly different ($p<0.001$). Values are represented as an average of 3 or 4 replicates±standard error.

TERMS

Unless otherwise explained, all technical and scientific terms used herein have the same meaning as commonly understood by one of ordinary skill in the art to which a disclosed invention belongs. The singular terms "a," "an," and "the" include plural referents unless context clearly indicates otherwise. Similarly, the word "or" is intended to include "and" unless the context clearly indicates otherwise. "Comprising" means "including." Hence "comprising A or B" means "including A" or "including B" or "including A and B."

Suitable methods and materials for the practice and/or testing of embodiments of the disclosure are described below. Such methods and materials are illustrative only and are not intended to be limiting. Other methods and materials similar or equivalent to those described herein can be used. For example, conventional methods well known in the art to which the disclosure pertains are described in various general and more specific references, including, for example, Sambrook et al., Molecular Cloning: A Laboratory Manual, 2d ed., Cold Spring Harbor Laboratory Press, 1989; Sambrook et al., Molecular Cloning: A Laboratory Manual, 3d ed., Cold Spring Harbor Press, 2001; Ausubel et al., Current Protocols in Molecular Biology, Greene Publishing Associates, 1992 (and Supplements to 2000); Ausubel et al., Short Protocols in Molecular Biology: A Compendium of Methods from Current Protocols in Molecular Biology, 4th ed., Wiley & Sons, 1999; Harlow and Lane, Antibodies: A Laboratory Manual, Cold Spring Harbor Laboratory Press, 1990; and Harlow and Lane, Using Antibodies: A Laboratory Manual, Cold Spring Harbor Laboratory Press, 1999, the disclosures of which are incorporated in their entirety by reference herein.

All publications, patent applications, patents, and other references mentioned herein are incorporated by reference in their entirety. Although methods and materials similar or equivalent to those described herein can be used to practice or test the disclosed technology, suitable methods and materials are described below. The materials, methods, and examples are illustrative only and not intended to be limiting.

Complementary: As used herein, "complementary" is a term that may be used to indicate a sufficient degree of complementarity such that stable and specific binding occurs between a compound of the invention and a target RNA molecule. Specific binding requires a sufficient degree of complementarity to avoid non-specific binding of the oligomeric compound to non-target sequences under conditions in which specific binding is desired, e.g., under physiological conditions in the case of in vivo assays, or in the case of in vitro assays, under conditions in which the assays are performed. The non-target sequences may differ by a certain number of nucleotides. In some embodiments, an RNAi compound is "complementary" to a target, e.g., a target mRNA, such that the RNAi compound silences production of protein encoded by the target mRNA.

RNA: The term "RNA interference" (RNAi) was coined after the discovery that injection of dsRNA into the nematode C. elegans leads to specific silencing of genes highly homologous in sequence to the delivered dsRNA (Fire et at, 1998). RNAi is closely linked to the post-transcriptional gene-silencing (PTGS) mechanism of co-suppression in plants and quelling in fungi (Catalanotto et al., 2000; Cogoni and Macino, 1999; Dalmay et al., 2000, Ketting and Plasterk, 2000; Mourrain et at, 2000; Smardon et al., 2000) and some components of the RNAi machinery are also necessary for post-transcriptional silencing by co-suppression (Catalanotto et al., 2000; Dernburg et at, 2000; Ketting and Plasterk, 2000). The topic has been reviewed extensively, see Bass, 2000; Bosher and Labouesse, 2000; Fire, 1999; Plasterk and Ketting, 2000; Sharp, 1999; Sijen and Kooter, 2000, see also the entire issue of Plant Molecular Biology, vol. 43, issue 2/3, (2000). In plants, in addition to PTGS, introduced transgenes can also lead to transcriptional gene silencing via RNA-directed DNA methylation of cytosines (see references in Wassenegger, 2000). Genomic targets as short as 30 bp are methylated in plants in an RNA-directed manner (Pelissier, 2000). DsRNA triggers the specific degradation of homologous RNAs only within the region of identity with the dsRNA (Zamore et al., 2000). The dsRNA is processed to 21-23 nt RNA fragments (Zamore et al., 2000). RNA molecules of similar size also accumulate in plant tissue that exhibits PTGS (Hamilton and Baulcombe, 1999).

Vector/Construct: Any nucleic acid that acts as a carrier for other (e.g., foreign) nucleic acid sequences that are not native to the vector. When introduced into an appropriate host cell, a vector may replicate itself (and, thereby, the foreign nucleic acid sequence) or express at least a portion of the foreign nucleic acid sequence. In one context, a vector is a linear or circular nucleic acid into which a nucleic acid sequence of interest is introduced (for example, cloned) for the purpose of replication (e.g., production) and/or manipulation using standard recombinant nucleic acid techniques (e.g., restriction digestion). A vector can include nucleic acid sequences that permit it to replicate in a host cell, such as an origin of replication. A vector can also include one or more selectable marker genes and other genetic elements known in the art. Common vectors include, for example, plasmids, cosmids, phage, phagemids, artificial chromosomes (e.g., BAC, PAC, HAC, YAC), and hybrids that incorporate features of more than one of these types of vectors. Typically, a vector includes one or more unique restriction sites (and in some cases a multi-cloning site) to facilitate insertion of a target nucleic acid sequence.

DESCRIPTION OF PREFERRED EMBODIMENTS

There are at least 16 structurally related *Aspergillus* aflatoxins that have been characterized. For example, 81 (AFB$_1$), B2 (AFB$_2$), G1 (AFG$_1$), and G2 (AFG$_2$) are the major aflatoxins that contaminate agricultural commodities.

The present invention features transgenic plant species engineered to inhibit aflatoxin production in *Aspergillus* by expressing RNAi against a gene required for aflatoxin biosynthesis. The present invention also features methods of producing said transgenic plant species, as well as compositions (e.g., tools, compounds, molecules, (e.g., RNAi cassettes, etc.), etc.) for the production of said transgenic plant species. For example, the present invention features transgenic maize plants or peanut plants comprising an RNAi construct, wherein the RNAi constructed is engineered to express RNAi against an *Aspergillus* aflatoxin biosynthesis gene, e.g., aflC. In some embodiments, the RNAi construct comprises an endosperm-specific RNAi suppression cassette. In some embodiments, the RNAi construct comprises a cassette targeted to the polyketide synthase aflatoxin biosynthesis gene (RNAi-aflC).

For reference, *Aspergillus parasitus* polyketide synthase (pKSL1, aflC) mRNA is shown below in Table 1 (genebank accession L42766). The bold sections in Table 1 represent the sections of the gene that were targeted with RNAi.

TABLE 1

*Aspergillus. parasitus* polyketide synthase (pKSL1) mRNA (L42766).
(SEQ ID NO: 1)

```
   1  tgcttccatc cagtttcaac aatctcatac cctatcccac aatggcccaa tcaaggcaac
  61  tctttctctt cggcgatcag acagccgatt ttgttcccaa gctccgcagt ttactatccg
 121  tccaggacag ccctattcta gccgcctttc ttgaccagtc ccactatgtc gtgcgagccc
 181  agatgctgca gagcatgaac acggttgatc acaagttggc tcgaaccgct gacctgcgcc
 241  aaatggtcca gaagtatgtc gacggcaaac tgaccctgc atttcgaacc gctccagtgt
 301  gcctctgcca gttgggatgc ttcatccggg aatatgagga atctggcaac atgtacccac
 361  agcccagtga cagctacgtg ctgggattct gcatgggttc cttggccgct gtggcggtaa
 421  gctgcagtcg ctccctgtca gagctgctgc ctatcgctgt acaaactgtg ttgattgcct
 481  Cccgcctcgg tctttgcgcc ctggagatgc gggatcgggt ggatgggtgt agcgatgatc
 541  gaggtgaccc ttggtctacc actgttcggg gtctggatcc ccagcaagct cgtgatcaga
 601  ttgaagtgtt ctgtcggacc acaaacgtac ctcagacaag gcgtccgtgg atcagctgca
 661  tctctaagaa tgccatcacc ctaagtagca gcccatccac tttgagggcg ttctgtgcga
 721  tgcctcagat ggcccagcac cggactgccc caattcccat ctgtttaccg gcccacaatg
 781  gcgccctctt cacgcaggca gataccacta ccatactaga cacgacgcct accactcctt
 841  gggagcaact gcccggccaa atacctcata tttcccatgt cacggggaat gtagtccaga
 901  cttccaacta ccgggacctt atagaggtag ccctgtctga gactctcttg gagcaagtgc
 961  gactagactt ggttgagact ggactgccac gccttttgca atctcgtcag tcaagagcg
1021  tcaccatcgt accattcttg acccgcacga atgagacaat gagcaacatt ctcccagaca
1081  gctttatcag tacagagaca aggactgaca ccggacgagc catcccagct tcaggtcgac
1141  caggcgcagg caagcgcaag ctggctattg tgtccatgtc ggggaggttc cctgaatcac
1201  cgaccaccga aagcttttgc gaccttctat acaaagggtt ggatgttgt aaagaggttc
1261  cccgtcgacg gtgggacatc aacacgcatg tggatcccag cgggaaagca cgaaacaaag
1321  gggctaccaa atggggctgc tggctagatt tctcaggcga ttttgatccc cgattctttg
1381  ggatctcgcc caaagaggcg ccacagatgg atccagctca gcgcatggcc ttgatgtcta
1441  cttacgaggc aatggagcgg gctggtttgg ttcccgacac cacgccgtcg acccagcgag
1501  accgcattgg ggtcttccac ggagtcacca gtaacgactg gatggagacc aatacagccc
1561  agaacattga cacatacttc atcaccggta gaaatcgggg gtttattccc gggcgcatta
1621  acttctgttt cgaatttgcc ggacccagct ataccaatga cacggcctgt tcatccagtc
1681  tagctgccat ccacctggcc tgcaattctc tctggcgggg cgactgtgac acggcggtgg
1741  caggaggaac taacatgatc tatactcctg atggtcacac aggattggac aaagggttct
1801  ctctttcccg gactggcaac tgcaaaccct acgacgacaa ggccgatggt tactgccgag
1861  ctgaggggt cgggacggtg ttcatcaaac ggctggaaga tgctctggca gataatgacc
1921  ccatccttgg cgttattcta gatgctaaaa ctaatcactc agccatgtcg gagtccatga
1981  ctcggccgca cgtgggcgcc caaatcgata acatgacggc ggcgctgaat accactggac
2041  tccatcccaa tgactttagc tacattgaga tgcatggcac tggcacccag gtaggggatg
2101  cggtggagat ggagtcagtc ctgtcggtgt ttgcgccgtc cgaaaccgcc agaaaggcgg
2161  atcagccact atttgtcggc tcagccaagg ccaacgtagg acatggagag ggagtgtctg
2221  gggttacgag ccttattaag gttctgatga tgatgcagca cgataccata cctcctcact
2281  gcggcatcaa accgggcagc aaaatcaacc gcaacttccc tgatcttgga gctcgcaatg
```

TABLE 1-continued

```
2341  tgcacatcgc ctttgaaccc aagccctggc cacgaacaca cactccgcgc agggtgctta
2401  tcaacaactt cagtgccgcg ggagggaata ctgccttgat agtggaagac gctccggagc
2461  gtcactggcc gacagagaag gatccgcgct ctagtcatat cgtcgccctg tctgcgcatg
2521  tggggcttc catgaaaacc aacctcgaac gactgcatca gtatctcctg aaaaaccccc
2581  acactgatct cgcgcagctg tcatatacta ctactgcgcg tcgatggcat tatctacacc
2641  gagtgagcgt cactggcgcg tctgttgaag aagtgactcg caagctagag atggccatac
2701  agaacgggga cggagtcagt cgacccaaaa gcaagccgaa gattctcttt gctttcacgg
2761  gacaagggtc tcaatatgca actatgggta agcaggtgta cgatgcgtat ccatctttca
2821  gagaggacct ggagaagttt gatcggttgg cgcaaagtca tggcttccct agctttcttc
2881  acgtctgtac ttcacctaaa ggggatgtgg aagagatggc tcccgttgtg gtgcaactgg
2941  ctatcacttg tctccaaatg gcccctacca acctcatgac ctccttcggg atccgtcccg
3001  atgtgacagt ggggcatagt ttgggtgaat ttgcagccct gtatgcggcg ggagttcttt
3061  cggcctcaga cgtcgtttac cttgttggtc aaagagcgga gctactccag gagcgctgcc
3121  aacgcgggac gcatgccatg ctggctgtga aagctacccc tgaagcgttg tcccaatgga
3181  tccaggatca tgactgtgag gtggcctgta ttaatggccc tgaagatacc gttctcagtg
3241  gcaccactaa gaatgttgcc gaggttcaac gcgctatgac ggacaacggg atcaaatgca
3301  cgctgttgaa actgccgttt gccttccatt ctgcccaggt gcaacctatt ctggacgact
3361  ttgaggcccc ggctcaggga gcgacatttg ccaagcctca actactaatt ctctctccct
3421  tgctgcggac agaaatccac gaacaaggcg tcgtgactcc atcatatgtc gcgcaacatt
3481  gtcgtcacac cgtagatatg gcccaagctt tgagatctgc tcgagaaaag ggactcatcg
3541  acgacaaaac cctcgtcatt gagctgggac cgaagccatt aatctcgggc atggtgaaaa
3601  tgacactggg agacaaaatt agcaccttac ccactctagc acctaacaag gccatttggc
3661  ccagcctgca gaagattctc acctcggtct acacgggtgg gtgggatatt aattggaaga
3721  aatatcacgc cccctttcgc ctcctcccaga aggtggtgga ctgccgagc tacggctggg
3781  attcgaagga ctactacatc ccgtatcagg gtgactggtg tctgcatcgc caccagcagg
3841  attgtaagtg cgccgctcct ggccacgaaa tcaaaacggc cgactaccaa gtgcctcctg
3901  agtccacgcc tcaccgtcca tccaagctgg accctagcaa ggaggccttc cccgaaatca
3961  agaccaccac gacactccat cgagtggtgg aagagacgac caaacctctg ggcgccaccc
4021  tagttgtgga gacagacata tctcggaagg atgtcaacgg cctcgctcga gggcaccttg
4081  tcgatgggat ccccttgtgt accccttcct tttatgctga catcgccatg caagtgggcc
4141  aatacagtat gcaacggctc cgtgcgggac atccggggc cggtgccata gatggccttg
4201  tggacgtgtc cgacatggtg gtggacaaag cgctggttcc ccatgggaag ggacctcaat
4261  tgctgcgcac gacgcttacc atggagtggc cgcccaaggc tgctgctact acgcgaagcg
4321  ccaaagtcaa attcgccacc tattttgccg atgggaagct cgatacggag catgccagct
4381  gtactgtcag attcacaagc gatgcacagt cgaaatctct acgccggtct gtgtccgagt
4441  acaaagaccca cattcgtcag ttacatgatg gccatgctaa gggacagttc atgcgataca
4501  ataggaagac cgggtacaag ctcatgagca gcatggctcg gtttaatccc gactacatgc
4561  tcctagatta tctggtgctg aacgaagcag agaacgaggc agcaagtggt gtagacttct
4621  cgttgggatc gtcggaaggc accttcgcag ctcacccagc tcacgtcgat gccatcactc
4681  aggtggccgg ctttgctatg aatgccaatg acaatgtcga cattgagaaa caggtcnacg
```

TABLE 1-continued

| | | | | | |
|---|---|---|---|---|---|
| 4741 | ttaatcacgg | ttgggactcg | ttccagatct | accaaccgct | ggataatagc aagtcttacc |
| 4801 | aggtctacac | caagatgggt | caagcgaagg | agaatgattt | ggtgcatggc gatgtggtag |
| 4861 | ttctggacgg | agaacaaatc | gttgctttct | tccgcggcct | tacgctgcga tcagttcctc |
| 4921 | gtggtgcact | gcgcgtcgtc | ctgcagacta | cagtgaaaaa | ggccgatcgc caactaggat |
| 4981 | ttaagacaat | gccgtcgccg | ccgccccga | caacgacaat | gccaatatcg ccttataaac |
| 5041 | cagctaatac | tcaggtttcc | agccaagcta | ttccagcaga | ggccactcat tctcacaccc |
| 5101 | cgccacagcc | aaagcattcc | ccggtaccgg | aaactgccgg | aagcgctcca gcggcaaaag |
| 5161 | gagtaggcgt | cagtaacgaa | aagttagatg | ctgtaatgcg | agtcgtttcg gaggagagtg |
| 5221 | gaattgccct | cgaggagctc | accgatgaca | gcaactttgc | tgacatgggc atcgactctc |
| 5281 | tgagttcaat | ggtcatcggg | agccgcttca | gagaggaccc | ggggctggac ccggggcctg |
| 5341 | agttttctct | tttcattgac | tgcactaccg | cgcgtgcctc | gaaagacttc atgttgggaa |
| 5401 | gcggggatgc | tggcagtggc | tccaatgtag | aagatcctcc | cccatcagct actcccggca |
| 5461 | tcaaccccga | aaccgattgg | tctagcagtg | cctctgatag | tattttcgcc agcgaagacc |
| 5521 | acggtcattc | gagtgagtcc | ggcgccgaca | ccggaagccc | gcctgcactt gatctgaagc |
| 5581 | cctactgccg | ccctcaact | tctgtcgtcc | tacaaggtct | acctatggtg gcgcggaaaa |
| 5641 | ctctgtttat | gctccctgat | ggcgggggt | ctgcgttctc | ctacgcctcc ctgccgcacc |
| 5701 | tcaaatcaga | tactgccgtt | gtgggcctga | attgcccta | tgctcgggat cccgagaaca |
| 5761 | tgaactgcac | acatggagct | atgattgaga | gcttttgcaa | tgagatccgg cggcgacagc |
| 5821 | cacggggccc | ctatcacctg | ggcggctggt | cgtccggtgg | tgcactcgct tacgtcgtgg |
| 5881 | ccgaggcact | tgttaaccaa | ggcgaggagg | tgcattcgtt | aatcatcatt gatgcgccta |
| 5941 | ttccccaagc | catggaacaa | cttccccgag | cattttacga | gcactgcaat agcattggat |
| 6001 | tgttcgctac | ccagccgggg | gctagtccgg | acggctcgac | tgagcctcca tcctacttaa |
| 6061 | tcccacactt | taccgctgtg | gtggatgtga | tgctggatta | caagctggcc ccgttgcatg |
| 6121 | cgcgccggat | gcccaaggtc | ggcatcgtct | gggcggcaga | tacagtcatg gacgagcggg |
| 6181 | acgctcccaa | gatgaaagga | atgcatttta | tgattcagaa | gcggacggaa tttggtcccg |
| 6241 | atgggtggga | tacgaccatg | cccggggcct | cgtttgacat | tgtccgagca gacggtgcta |
| 6301 | atcattttac | gttgacgcaa | aaggaacatg | tctctataat | tagcgatctg atcgaccggg |
| 6361 | tcatggctta | gcaaaccccg | ttttggtggg | ccgcccgcat | acttacaact attatggctc |
| 6421 | ctggcggagg | aaggaagcaa | gggcgtgttt | ttcagttgtt | gccgctgtta gaaatgacga |
| 6481 | aactgtggtt | tacaaacttg | ttttacaggg | ctcattctgt | atattgattc caattccata |
| 6541 | aataggtatt | ttaacgatga | tagcataccc | accattttag | acaattagtc tccc |

Table 2 below shows a synthetic sequence engineered for the RNAi construct. The sequence comprises the three sections of the gene targeted for RNAi (see Table 1). Slashes (/) are used for clarity to show the separation of the sections of the target gene (e.g., the sequence in Table 2 comprises three sections of the target gene). In some embodiments, the sections of the target gene are connected together without additional (e.g., linking) nucleotides. In some embodiments, the sections of the target gene are separated by one or more linking nucleotides.

TABLE 2

Synthetic RNAi sequence (SEQ ID NO: 2)

Tctagactcga[gtatgcggcgggagttcttttcggcctcagacgtcgttt
accttgttggtcaaagagcggagctactccaggagcgctgccaacgcggg
acgcatgccatgctggctgtgaaagctaccctgaagcgttgtcccaatg
gatccaggatcatgactgtgaggtggcctgtattaatggccctgaagata
ccgttctcagtggca][agacccacattcgtcagttacatgatggccatg
ctaagggacagttcatgcgatacaataggaagaccgggtacaagctcatg
agcagcatggctcggtttaatcccgactacatgctcctagattatctggt TABLE 2-continued Synthetic RNAi sequence (SEQ ID NO: 2)

gctgaacgaagcagagaacgaggcagcaagtggtgtagacttctcgttgg
gatcgtcggaaggca][tccccaagccatggaacaacttccccgagcatt
ttacgagcactgcaatagcattggattgttcgctacccagccgggggcta
gtccggacggctcgactgagcctccatcctacttaatcccacactttacc
gctgtggtggatgtgatgctggattacaagctggccccgttgcatgcgcg
ccggatgcccaaggtcg]actagtaagctt The present invention is not limited to the example shown in Table 2 (SEQ ID NO: 2) (or the examples shown in Table 4 (SEQ ID NO: 6-8)). For example, other nucleotides in the gene may be targeted (for example, as long as they don't have significant homology to sequences in the expressing plant or possible consumers). For example, while SEQ ID NO: 2 comprises three sections corresponding to nucleotides 3041-3250, 4444-4631, and 5942-6141 of SEQ ID NO: 1, the sections of the target gene may be selected from other nucleotides of SEQ ID NO: 1. In some embodiments, a section comprises a sequence (between 100 to 300 nucleotides) starting from any nucleotide, e.g., nucleotide 1, 2, 3, 4, 5, 6, 7, 8, 9, 10, 20, 30, 40, 50, 60, 70, 80, 90, 100, 110, 120, 130, 140, 150, 160, 170, 180, 190, 200, 300, 400, 500, 600, 700, 800, 900, 1000, 1100, 1200, 1300, 1400, 1500, 1600, 1700, 1800, 1900, 2000, 3000, 4000, 5000, 6000, etc., e.g., a nucleotide selected from nucleotides 1-500, 500-1000, 1000-1500, 1500-2000, 2000-2500, 2500-3000, 3000-3500, 3500-4000, 4000-4500, 4500-5000, 5000-5500, 5500-6000, 6000-6594, etc. In some embodiments, the combination of sections used for the template span 25% of the gene sequence. In some embodiments, the combination of sections used for the template span 30% of the gene sequence. In some embodiments, the combination of sections used for the template span 40% of the gene sequence. In some embodiments, the combination of sections used for the template span 50% of the gene sequence. In some embodiments, the combination of sections used for the template span more than 50% of the gene sequence. In some embodiments, the combination of sections used for the template span at least 75% of the gene sequence. In some embodiments, the combination of sections used for the template span at least 80% of the gene sequence. In some embodiments, the combination of sections used for the template span at least 90% of the gene sequence. In some embodiments, the combination of sections used for the template span at least 95% of the gene sequence. In some embodiments, a section comprises SEQ ID NO: 3, e.g., nucleotides 12-214 of SEQ ID NO: 2. In some embodiments, a section comprises SEQ ID NO: 4, e.g., nucleotides 215-412 of SEQ ID NO: 2. In some embodiments, a section comprises SEQ ID NO: 5, e.g., nucleotides 413-612 of SEQ ID NO: 2.

TABLE 3

| SEQ ID NO: | Sequence |
|---|---|
| 3 | gtatgcggcgggagttctttcggcctcagacgtcgtttacct tgttggtcaaagagcggagctactccaggagcgctgccaacg cgggacgcatgccatgctggctgtgaaagctacccctgaagc gttgtcccaatggatccaggatcatgactgtgaggtggcctg tattaatggccctgaagataccgttctcagtggca |
| 4 | agacccacattcgtcagttacatgatggccatgctaagggac agttcatgcgatacaataggaagacgggtacaagctcatga gcagcatggctcggtttaatcccgactacatgctcctagatt atctggtgctgaacgaagcagagaacgaggcagcaagtggtg tagacttctcgttgggatcgtcggaaggca |
| 5 | tccccaagccatggaacaacttccccgagcattttacgagca ctgcaatagcattggattgttcgctacccagccgggggctag tccggacggctcgactgagcctccatcctacttaatcccaca ctttaccgctgtggtggatgtgatgctggattacaagctggc cccgttgcatgcgcgccggatgcccaaggtcg |

Table 4 shows non-limiting examples of alternative synthetic RNAi sequences, e.g., alternative sequences of sections used for the RNAi construct, wherein the RNAi sequences are at least 90% homologous to the target sequences, e.g., at least 90% homologous to SEQ ID NO: 3. The nucleotides in bold represent the differences from the actual target nucleic acid sequence (e.g., aflC). The present invention is not limited to the examples shown in Table 3; the examples are for the purposes of describing sequences that have at least 90% homology to the target sequence (e.g., aflC). Note that the sequences below only comprise one section of the aflC gene. As previously discussed, in some embodiments, the RNAi sequence may comprise two or more sections of the target gene. In some embodiments, the RNAi sequence may comprise three or more sections of the gene.

TABLE 4

| Example | Sequence of Synthetic RNAi | % Homology to Actual Gene Sequence |
|---|---|---|
| 1 (SEQ ID NO: 3) | gtaagcggcgggacttctctcggcctcagccgtcgtttacct tcttggtcaaagagcggcgctactccaggagcgctcccaacg cgggacgcttgccatgctgggtgtgaaagctaccccggaagc gttgtctcaatggatccaggatgatgactgtgagctggcctg aactaattgccctgaagagaccgttctcactggca | 92 |
| 2 (SEQ ID NO: 4) | gtatccggcgggagttctttcggccacagacgtcggttacct tgttggtcaaagagcggagctactccaggagcgctgccaacg cgggtcgcatgcaatgctggctgtgaaagctacccctgaagg gttctcccaatggatccaggatcatgactgtggggtggcctg tattaaaggccctgaagataccgttctcagtggca | 95 |

TABLE 4-continued

| Example | Sequence of Synthetic RNAi | % Homology to Actual Gene Sequence |
|---|---|---|
| 3 (SEQ ID NO: 5) | gaatgcggcgggagttctttcggcctcagacgacgtttacct tgttggtcaaacagcggagccactccaggagcgctgccaacg cgggacgcatgccatgctggctgtgaaagctacccctgaagc gttgtcccaatggatccaggatcatgactgtgaggtggcctg tattaatggccctgaagataccgttctcagtggca | 99 |

The dsRNA of the invention may optionally comprise a single stranded overhang at either or both ends. In some embodiments, the double-stranded structure may be formed by a single self-complementary RNA strand (e.g., forming a hairpin loop) or two complementary RNA strands, RNA duplex formation may be initiated either inside or outside the cell. When the dsRNA of the invention forms a hairpin loop, it may optionally comprise an intron and/or a nucleotide spacer, which is a stretch of nucleotides between the complementary RNA strands, to stabilize the hairpin sequence in cells. The RNA may be introduced in an amount that allows delivery of at least one copy per cell. Higher doses of double-stranded material may yield more effective inhibition.

As used herein, the term "nucleic acid construct" means a nucleic acid molecule capable of transporting another nucleic acid to which it is linked. One type of nucleic acid construct is a vector, which can be a transformation vector or an expression vector. Another type of nucleic acid construct of this invention is a "plasmid," which refers to a circular double stranded nucleic acid loop into which additional nucleic acid segments can be ligated. Another type of nucleic acid construct is a viral vector, wherein additional nucleic acid segments can be ligated into a viral genome. Certain vectors are capable of autonomous replication in a plant cell into which they are introduced. Other vectors are integrated into the genome of a plant cell upon introduction into the plant cell, and are then replicated along with the plant cell genome. Moreover, certain vectors can direct the expression of genes or coding sequences to which they are operatively linked. Such vectors are referred to herein as "expression vectors." In some embodiments of this invention, an expression vector can be a viral vector (e.g., potato virus X; tobacco rattle virus; Geminivirus).

An expression vector of the invention can comprise a nucleic acid of the invention in a form suitable for expression of the nucleic acid in a plant cell, which means that the expression vector includes one or more regulatory sequences, selected on the basis of the plant cells to be used for expression, which is operatively linked to the nucleic acid sequence to be expressed. With respect to an expression vector, "operatively linked" is intended to mean that the nucleotide sequence of interest is linked to the regulatory sequence(s) in a manner which allows for expression of the nucleotide sequence (e.g., in a plant cell when the vector is introduced into the plant cell). The term "regulatory sequence" is intended to include promoters, enhancers, and other expression control elements (e.g., polyadenylation signals) as are well known in the art. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of dsRNA desired, etc. The expression vectors of the invention can be introduced into plant cells to thereby produce dsRNA molecules encoded by nucleic acids as described herein.

In some embodiments, the expression vector can comprise a regulatory sequence operably linked to a nucleotide sequence that is a template for one or both strands of the claimed dsRNA molecules. In one embodiment, the nucleic acid molecule further comprises a promoter flanking either end of the nucleic acid molecule, wherein the promoters drive expression of each individual DNA strand, thereby generating two RNAs that hybridize and form the dsRNA. In another embodiment, the nucleic acid molecule comprises a nucleotide sequence that is transcribed into both strands of the dsRNA on one transcription unit, wherein the sense strand is transcribed from the 5' end of the transcription unit and the antisense strand is transcribed from the 3' end, wherein the two strands are separated, e.g., by about 3 to about 500 basepairs, and wherein after transcription, the RNA transcript folds on itself to form a hairpin. In accordance with the invention, the spacer region in the hairpin transcript can be any nucleic acid fragment.

In some embodiments of this invention, the introduced nucleic acid molecule may be maintained in the plant cell stably if it is incorporated into a non-chromosomal autonomous replicon or integrated into the plant chromosomes. Alternatively, the introduced nucleic acid molecule may be present on an extra-chromosomal non-replicating vector and be transiently expressed or transiently active. Whether present in an extra-chromosomal non-replicating vector or a vector that is integrated into a chromosome, the nucleic acid molecule can be present in a plant expression cassette. A plant expression cassette can contain regulatory sequences that drive ge e expression in plant cells that are operably linked so that each sequence can fulfill its function, for example, termination of transcription by polyadenylation signals. In some embodiments, polyadenylation signals can be those originating from *Agrobacterium tumefaciens* t-DNA such as the gene known as octopine synthase of the Ti-plasmid pTiACH5 (Gielen et al. EMBO J. 3:835 (1984)) or functional equivalents thereof, but also all other terminators functionally active in plants are suitable. A plant expression cassette of this invention can also contain other operably linked sequences like translational enhancers such as the overdrive-sequence containing the 5'-untranslated leader sequence from tobacco mosaic virus enhancing the polypeptide per RNA ratio (Gallie et al. Nucl. Acids Research 15:8693-8711 (1987)).

A nucleic acid molecule of this invention can be introduced into a cell by any method known to those of skill in the art. In some embodiments of the present invention, transformation of a plant cell of this invention can comprise nuclear transformation. In other embodiments, transformation of a plant cell of this invention can comprises plastid transformation (e.g., chloroplast transformation).

Procedures for transforming plants are well known and routine in the art and are described throughout the literature. Non-limiting examples of methods for transformation of plants include transformation via bacterial-mediated nucleic acid delivery (e.g., via Agrobacteria), viral-mediated nucleic acid delivery, silicon carbide or nucleic acid whisker—mediated nucleic acid delivery, liposome mediated nucleic acid delivery, microinjection, microparticle bombardment, calcium-phosphate-mediated transformation, cyclodextrin-mediated transformation, electroporation, nanoparticle-mediated transformation, sonication, infiltration, PEG-mediated nucleic acid uptake, as well as any other electrical, chemical, physical (mechanical) and/or biological mechanism that results in the introduction of nucleic acid into the plant cell, including any combination thereof. General guides to various plant transformation methods known in the art include Miki et al. ("Procedures for Introducing Foreign DNA into Plants" in Methods in Plant Molecular Biology and Biotechnology. Glid B. R. and Thompson, J. E., Eds. (CRC Press, Inc., Boca Raton, 1993), pages 67-88) and Rakowoczy-Trojanowska {Cell. Mol. Biol. Lett. 7:849-858 (2002)).

Thus, in some embodiments, the introducing into a plant, plant part and/or plant cell is via bacterial-mediated transformation, particle bombardment transformation, calcium-phosphate-mediated transformation, cyclodextrin-mediated transformation, electroporation, liposome-mediated transformation, nanoparticle-mediated transformation, polymer-mediated transformation, virus-mediated nucleic acid delivery, whisker-mediated nucleic acid delivery, microinjection, sonication, infiltration, polyethyleneglycol-mediated transformation, any other electrical, chemical, physical and/or biological mechanism that results in the introduction of nucleic acid into the plant, plant part and/or cell thereof, or any combination thereof.

*Agrobacterium*-mediated transformation is a commonly used method for transforming plants, in particular, dicot plants, because of its high efficiency of transformation and because of its broad utility with many different species. *Agrobacterium*-mediated transformation typically involves transfer of the binary vector carrying the foreign DNA of interest to an appropriate *Agrobacterium* strain that may depend on the complement of vir genes carried by the host *Agrobacterium* strain either on a co-resident Ti plasmid or chromosomally (Uknes et al. (1993) Plant Cell 5:159-169). The transfer of the recombinant binary vector to *Agrobacterium* can be accomplished by a triparental mating procedure using *Escherichia coli* carrying the recombinant binary vector, a helper *E. coli* strain that carries a plasmid that is able to mobilize the recombinant binary vector to the target *Agrobacterium* strain. Alternatively, the recombinant binary vector can be transferred to *Agrobacterium* by nucleic acid transformation (Hofgen & Willmitzer (1988) Nucleic Acids Res. 16:9877).

Transformation of a plant by recombinant *Agrobacterium* usually involves co-cultivation of the *Agrobacterium* with explants from the plant and follows methods well known in the art. Transformed tissue is regenerated on selection medium carrying an antibiotic or herbicide resistance marker between the binary plasmid T-DNA borders.

Another method for transforming plants, plant parts and plant cells involves propelling inert or biologically active particles at plant tissues and cells. See, e.g., U.S. Pat. Nos. 4,945,050; 5,036,006 and 5,100,792. Generally, this method involves propelling inert or biologically active particles at the plant cells under conditions effective to penetrate the outer surface of the cell and afford incorporation within the interior thereof. When inert particles are utilized, the vector can be introduced into the cell by coating the particles with the vector containing the nucleic acid of this invention. Alternatively, a cell or cells can be surrounded by the vector so that the vector is carried into the cell by the wake of the particle. Biologically active particles (e.g., dried yeast cells, dried bacterium or a bacteriophage, each containing one or more nucleic acids sought to be introduced) also can be propelled into plant tissue.

Thus, in particular embodiments of the present invention, a plant cell can be transformed by any method known in the art and as described herein and intact plants can be regenerated from these transformed cells using any of a variety of known techniques. Plant regeneration from plant cells, plant tissue culture and/or cultured protoplasts is described, for example, in Evans et al. (Handbook of Plant Cell Cultures, Vol. 1, MacMillan Publishing Co. New York (1983)); and Vasil I. R. (ed.) (Cell Culture and Somatic Cell Genetics of Plants, Acad. Press, Orlando, Vol. I (1984), and Vol. II (1986)). Methods of selecting for transformed transgenic plants, plant cells and/or plant tissue culture are routine in the ait and can be employed in the methods of the invention provided herein.

Likewise, the genetic properties engineered into the transgenic seeds and plants, plant parts, and/or plant cells of the present invention described above can be passed on by sexual reproduction or vegetative growth and therefore can be maintained and propagated in progeny plants. Generally, maintenance and propagation make use of known agricultural methods developed to fit specific purposes such as harvesting, sowing or tilling.

In some embodiments, a nucleotide sequence therefore can be introduced into the plant, plant part and/or plant cell in any number of ways that are well known in the art. The methods of the invention do not depend on a particular method for introducing one or more nucleotide sequences into a plant, only that they gain access to the interior of at least one cell of the plant.

In some embodiments, the present invention provides a crop comprising a plurality of any transgenic plant of this invention, planted together in an agricultural field.

Example 1

Example 1 describes the production of transgenic plants of the present invention, e.g., aflatoxin-free transgenic peanuts/maize (e.g., production of *Aspergillus* resistant aflatoxin-free transgenic peanut/maize by co-expressing, individually and together, the cell-penetrating antifungal plant defensing RNAi suppression cassette directed against an aflatoxin biosynthesis gene). The present invention is not limited to the methods, systems, and components described herein.

Transgenic maize plants can be transformed and regenerated expressing an endosperm-specific RNAi suppression cassette targeted to the polyketide synthase aflatoxin biosynthesis gene (RNAi aflC). Transgenic peanut plants can be transformed and regenerated expressing a seed-specific RNAi suppression cassette targeted to the polyketide synthase aflatoxin biosynthesis gene (RNAi aflC). The resultant transgenic plants (e.g., maize kernels, peanut seeds) can be analyzed for *Aspergillus* resistance and aflatoxin production compared to nontransgenic tissue.

Figure 2:
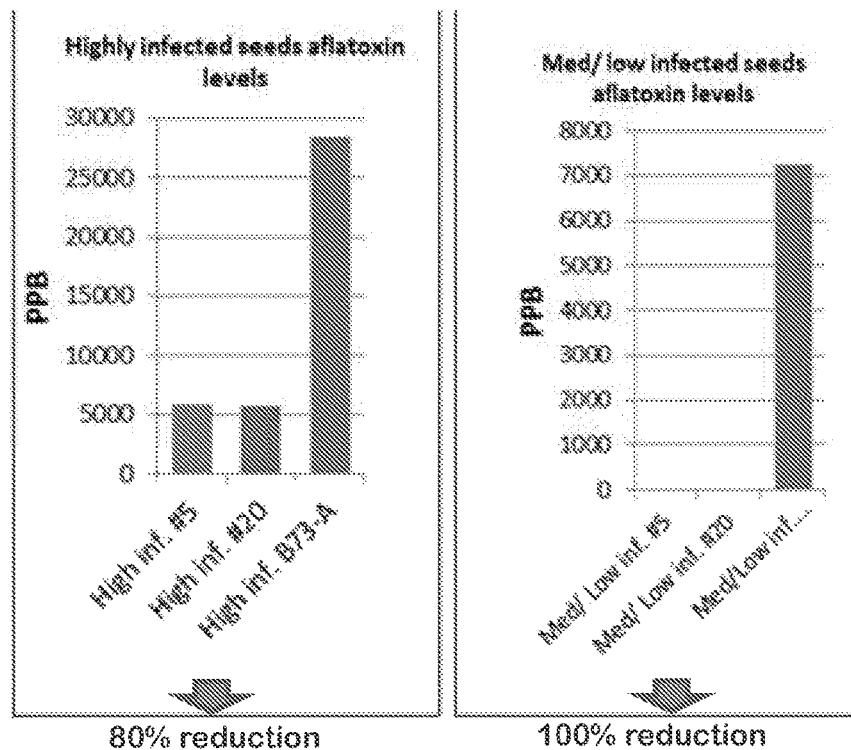
Figure 3:
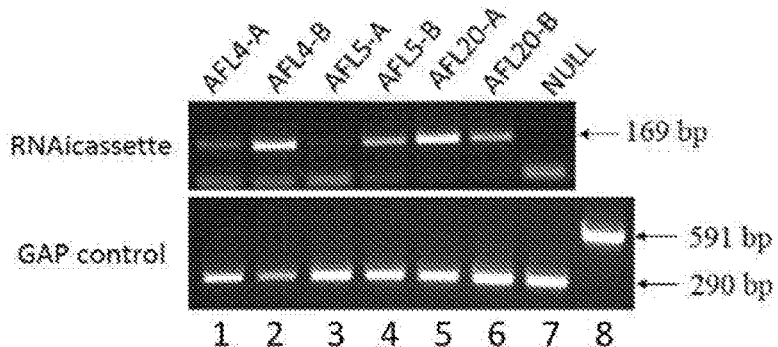

RNAi aflC Transgenic Maize and Peanut Plants have been Regenerated:

Aflatoxin biosynthesis has been proposed to involve at least 23 enzymatic reactions (see FIG. 2). Many of the aflatoxin pathway genes and their corresponding enzymes have been characterized. Sterigmatocystin is the ultimate precursor of all aflatoxin biosynthesis so impeding its production would preclude production of aflatoxins. The first dedicated step in the production of sterigmatocystin is the formation of polyketide from acetate, and three enzymes catalyze this: two fatty acid syntheses and a polyketide synthase. The polyketide synthase aflC (pksA) is a unique enzyme in this pathway and therefore is a candidate to target by RNAi technology. The aflC polyketide synthase gene has been cloned (Genbank Z47198, L42765, L42766) from both *A. flavus* and *A. parasiticus* and it is a large, over 7 kb, gene encoding for a 2109 amino acid protein. Of the 24 putative *A. flavus* polyketide syntheses only aflC (pksA) has been experimentally characterized.

The present invention extended recent scientific findings that small non-coding RNA molecules (siRNA) are able to pass between plants and their fungal pathogens. RNAi cassettes were produced that target a pivotal step in the aflatoxin biosynthesis pathway of *Aspergillus* and this cassette was expressed in stably transformed maize and peanut plants in relevant tissue. It was targeted to suppress the aflC polyketide synthase gene as it is an early step in the pathway to all aflatoxin compounds and it is very large and specific in sequence to the fungal pathogen; that is, there is no significant homology to the *Aspergillus* aflC gene in the maize or peanut genome or any possible consumer genome (e.g., humans, cattle, pigs, etc.). Since the gene is 7 Kb and in some embodiments, the expression is completely suppressed (not just a truncated version that may still partially function), three 200 bp sections of the polyketide aflC gene were suppressed simultaneously (see FIG. 1A). Without wishing to limit the present invention to any theory or mechanism, it is believed that the use of three sections of the gene for suppression would ensure its complete silencing. The sequences chosen to use in the RNAi polyketide synthase construct do not have any homology to sequences within the host plant genomes or downstream consumers (as the intention is to specifically suppress the production of the *Aspergillus* polyketide synthase gene and to cause no gene regulation disruption in the crops or consumers). FIG. 1B shows a detailed schematic of a cassette of the present invention. The present invention is not limited to the components or configurations shown in FIG. 1B.

Two plant expression cassettes were constructed using the RNAi polyketide synthase: for maize the RNAi was placed under the 1.1 kb zein endosperm-specific promoter in a vector with bialaphos resistance; for peanut, the RNAi was placed under the 1 kb glycinin cotyledonary-specific promoter in a vector with kanamycin resistance. Maize transgenic plants were obtained via *Agrobacterium* transformation of a B73 hybrid line. There were nine independently produced lines in the T2 generation. Two lines have been confirmed to be homozygous.

As peanut transformation is not as established as maize transformation it took nearly a year to produce PCR-positive transgenic peanut plantlets via *Agrobacterium* mediated transformation. The regeneration of roots from positive peanut cultures was problematic. It was surprisingly discovered that regeneration could be successful when using a step involving activated charcoal to absorb residual hormones used in the shoot-induction media steps. The present invention is not limited to these methods. For example, in some embodiments, grafting of transgenic shoots to nontransgenic peanut roots may be employed, e.g., to overcome the rooting problem.

RNAi aflC maize kernels display noteworthy reduction in aflatoxin post *Aspergillus* infection compared to nontransgenic control. Two lines (of transgenic RNAi aflC maize lines in the T2 generation) have progressed to homozygosity.

To simulate an infection of aflatoxin-producing *Aspergillus* in maize growing in a field, preliminary testing has been performed on developing kernels on cobs on plants growing in a contained greenhouse. The procedure involves inoculating ~10,000 spores in 10 mL suspension of *A. flavus* AF13 (a known high producing aflatoxin isolate) into both RNAi aflC lines and nontransgenic control using a cork borer. The protocol is outlined as Atehnkeng et al., 2008 *Food Additives and Contaminants Part A* 25:1264. Fertilized cobs from two RNAi aflC lines (line #5 homozygote: line #20 segregating) and nontransgenic B73 cuitivar all at R2 development (10 days after pollination) were infected. The infection was allowed to proceed for 1 wk. Kernels around the point of infection were harvested and assayed as above for aflatoxin load by TLC. Kernels were grouped from each infected cob by the following categories: damaged (physically damaged by injection), highly infected (extensive fungal growth), medium-low infected (less fungal growth), no infection (no visual fungal growth). Kernels from the groupings were collectively weighed and used as starting material for the extraction and analysis of aflatoxin. FIG. 2 shows preliminary results of the aflatoxin TLC readings.

The aflatoxin TLC analysis shows a reduction in aflatoxin accumulated in *Aspergillus*-infected RNAi aflC maize kernels compared to control nontransgenic kernels. In both the visual grouping of highly infected kernels and medium-low infected kernels, the RNAi aflC lines tested had ~80% reduction and non-detectable toxin levels, respectively. A number of kernels from each category were pooled, weighed before aflatoxin extraction and detection. The pooling of the kernels aids in the reduction of the variation seen in fungal infection within individual kernels. The limit of detect for this TLC fluorescence method is 20 ppb. Maize kernels infected in this manner typically produce 30,000 ppb aflatoxin and a comparable aflatoxin level in the nontrangenic maize highly infected kernels was seen, giving credibility that the assay was conducted correctly.

Example 2

Example 2 describes examples of RNAi cassette production and production of transgenic plants. The present invention is not limited to the methods, systems, and components described herein.

An RNAi cassette consisting of 3 head-to-tail sections of the *Aspergillus* aflC gene was constructed to ensure the fungal transcript was fully targeted and degraded by suppression. The RNAi cassette was expressed in a kernel-specific manner in transgenic maize (see FIG. 1C). A 1.1 kb gamma-zein endosperm-specific promoter was used to direct expression of the RNAi cassette targeting suppression of the fungal polyketide synthase gene in a vector having bialaphos resistance as a plant selectable marker. Maize transgenic plants were obtained via *Agrobacterium*-mediated transformation of a B73 hybrid line. Transgenic maize lines were grown to the T3 homozygous generation by repeated rounds of regeneration and molecular analysis. Plants were screened by genomic PCR for the presence of the selectable marker gene as well as leaf painting assays (3 mg/ml glufosinate ammonium) to determine the expression of the bialaphos resistant selectable marker. Expression of the RNAi cassette was determined by RT-PCR analysis of cDNA produced from total RNA extracted from 10-12 day post pollination kernels (see FIG. 3). Shown is the presence of a 169 bp amplicon in the RNAiAFL transgenic samples tested (lines 4, 5, 20) and not in segregating null control kernels indicating expression of the inserted RNAi cassette in the transgenic lines tested. An internal maize gene, GAP, was amplified as a control. Genomic DNA amplification using the GAP primers will produce a 591 bp amplicon (lane 8) which cDNA amplification will produce a 290 bp amplicon. The 290 bp amplicon present in the transgenic samples indicates that there was no contaminating genomic DNA present in the samples to indicate the expression of the inserted RNAiAFL cassette.

Figure 4:
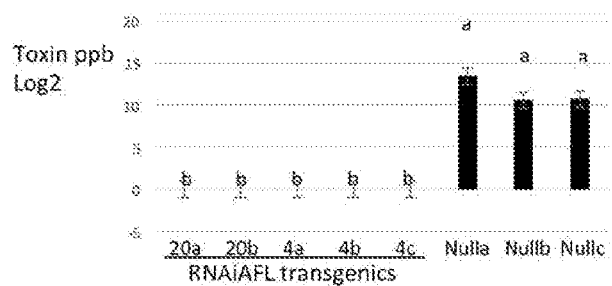

Transgenic RNAi expressing lines were infected with toxin-producing *Aspergillus* strain and subsequent toxin detection and quantification to assess if the inserted RNAi cassette was successful and capable of suppression of aflatoxin production. Kernels from the RNAiAFL transgenic maize plants display non-detectable levels of aflatoxin post *Aspergillus* infection compared to non-transgenic null controls (see FIG. 4). To simulate an infection of aflatoxin-producing *Aspergillus* in maize, a pathogen challenge was performed on developing kernels on cobs on plants growing in a contained greenhouse. The procedure involves inoculating ~10,000 spores in 10 mL suspension of *A. flavus* AF13 (a high producing aflatoxin isolate) into two RNAiAFL lines (4, 20) and segregating null controls using a cork borer. Briefly, fertilized cobs from plants from two homozygous RNAiAFL lines and three null B73 hybrid controls all at R2 development (10 days after pollination) were infected. The infection was allowed to proceed for 1 month. Kernels around the point of infection were harvested (~5-6 kernels/infection), combined and assayed for aflatoxin load by TLC. FIG. 4 shows the results of the aflatoxin TLC readings (graphic log 2 scale) (raw data not shown). The lowest limit of detection for this TLC fluorescence method is ~90 ppb. Three different plants of RNAiAFL4 were infected and assayed along with 2 plants of RNAiAFL20 and 3 segregating nontransgenic plants of the same cultivar (nulls). RNAiAFL4, for example, had 3 plants (AFL-4a, b, c) having 3-4 infections each (FIG. 4). Although there is considerable variability from plant-to-plant in the extent of fungal growth, the results consistently show null plants displaying toxin loads of hundreds-thousands ppb while no toxin can be detected in any of the RNAiAFL transgenic lines. Gene expression analysis of DNA isolated from infected material testing both a fungal gene (the suppression targeted polyketide synthase gene) and maize gene (glyceraldehyde-3 phosphate dehydrogenase) quantified via real time PCR shows that comparable fungal tissue, indicative of fungal growth, is present in transgenic maize kernels with no toxin detected (FIG. 4). The results of the aflatoxin assays indicate that RNAi suppression cassettes expressed in crop plants is effective to eliminate aflatoxin production in infected maize.

Construction of RNAi Polyketide Synthase (aflC) Cassette

Synthetic DNA was produced to incorporate 3 tandem sections of the polyketide synthase (aflC) mRNA from *Aspergillus* parasitus that would constitute the arms of the RNAi silencing cassette. A 606 bp chimeric synthetic fragment homologous to the aflC gene consisted of 5' restriction enzyme sites XbaI and XhoI followed by a 209 bp from nucleotide regions 3041-3250, 197 bp from regions 4444-4641, 00 bp from regions 5942-6142 (numbering according to Genbank accession L42766), with 3' HindIII and SpeI restriction sites. Both the synthetic DNA and plasmid containing a constructed intron, pkan-intron1 were double digested with XhoI/SpeI and ligated. After confirmation of the first arm of the synthetic DNA adjacent to the intron was confirmed by digests, the second arm was placed inverted by the double digest of XbaI/HindIII. Confirmation of both arms around the intron were confirmed by digestion and referred to as phairpinaflC. The 1.1 kb g zein promoter from maize (kindly provided by K. Wang, Iowa State University), was moved into the pMON999 vector by double digest of PstI/EcoRI. The pzein/MON999 plasmid was then digested with XbaI while the phairpinaflC digested with NotI, both blunted by T4 DNA polymerase. The blunt-end ligation of the liberated 1.8 kb phairpin placed the RNAi cassette between the g zein promoter and NOS terminator. Insertion of the cassette and its correct orientation in reference to the regulatory elements was confirmed by sequencing using independently a g zein promoter primer (5'GATCCCATCAAGCTTATCGATAC3', SEQ ID NO: 9) or NOS terminator primer (5'CCAAATGTTTGAACGATCGGG 3', SEQ ID NO: 10). The gene expression cassette zein::hairpinaflC was then placed by NOT1 digest and T4 DNA polymerase blunt end into SmaI digested pTF101.1, an *Agrobacterium* binary vector harboring bar resistance (phosphinothricin acetyltransferase) under the enhanced 35S CaMV promoter (Gateway). The resultant cassette is hereby referred to as RNAiAFL (see FIG. 1C). All enzymes were used as according to manufacturer's instructions and purchased from New England Biolabs.

Transgenic Maize Production

Maize (*Zea mays* Hill hybrid A188 and B73 background) was transformed with pRNAiAFL construct via *Agrobacterium*-mediated transformation 2 by the Iowa State Plant Transformation Facility (http://agron-www.agron.iastate.edu/ptf/). Nine bialophos resistant lines were received as plantlets and regenerated and screened by both molecular polymerase chain reaction to detect the zein::RNAiAFL construct with the genomic DNA (data not shown) and by leaf painting assays. The tips of young maize plantlets, 1.5 inch adaxial tip surface of fully expanded leaf of 8-10 days old seedlings, were sprayed with a glufosinate ammonium (3 mg/ml; Oakwood Products) with the sprayed area marked with pen. Glufosinate resistance was scored visually 7 days after painting. Plantlets expressing the Bar gene displayed good resistance with no observable marks in the sprayed area after 7 days while segregating null plantlets displayed necrosis of the painted area as soon as 1-2 days after application. Three lines were grown to homozygosity by repetitive self-pollination and glufasinate leaf painting assays.

RNAiAFL Expression in Transgenic Maize

For expression analysis of RNAiAFL transcript, three homozygous transgenic lines, AFL4, AFL5 and AFL20 and a non-transgenic (null) were used. Kernels of stage 13-15 DAP were harvested and flash frozen in liquid nitrogen. RNA was extracted with TRIzol LS Reagent (Ambion-Thermo Fisher Scientific) from 6 kernels ground to fine powder using mortar and pestle and ~100 mg for each preparation. For each transgenic and non-transgenic lines two biological replicates were performed. DNase treatment was performed on ~25 μg total RNA in 50 μl total volume using 0.1 volume 10×TURBO DNase Buffer and 1 μL (2 U) TURBO DNase as suggested for TURBO DNA-free Kit (Ambion-Thermo Fisher Scientific) and incubated 37° C. for 20-30 min. The RNA samples were then incubated with 5 μL of DNase Inactivation Reagent and incubated for 5 min at room temperature. Upon Centrifugation the DNA-free total RNA were used for reverse transcription. For reverse transcription RevertAid First Strand cDNA Synthesis Kit (Thermo Scientific) was used. For this ~1 µg DNA free RNA was mixed with 1 µl random primers and 9 µl 2M Betaine monohydrate (Fluka-Sigma-Aldrich) and heat denatured RNA was used for 1st strand synthesis using components as suggested at 25° C. for 5 min, 45° C. for 1 hr followed by heat inactivation at 72° C. for 5 min. The 5 µL volume from 0.1× diluted cDNA was used for PCR analysis using 0.4 mM each of forward primer qRT2RSeg1 (5-GTAGCTTTGACA-GCCAGCAT-3', SEQ ID NO 11) corresponding to segment 1 of Right arm and, and reverse primer NosSeq (5'CCAAAT-GTTTGAACGATCGGG-3', SEQ ID NO: 12) corresponding to NOS terminator sequences. The reaction mixture included 1×PCR buffer, 0.2 mM each dNTPs, and 2.5 U of Taq DNA polymerase (NEB) and, 50% volume of 2M Betaine. As an internal control, oligonucleotides ZmGAP_EX8_5' 5'(TGTGGATGTCTCGGTTGTTGA)3' (SEQ ID NO: 13) ZmGAP_EX10_3' 5'(CTTGAACAT-GTGGCGGATCAG)3' (SEQ ID NO: 14), corresponding to housekeeping gene GADPH (Genbank X15596.1) were used with expected amplicon sizes of 591 and 290 with genomic DNA and cDNA, respectively. The PCR cycles were set as 94° C. for 2 min followed 34 cycle of 94° C. for 30 sec, 53° C. for 30 sec and 72° C. for 1 min. The amplified products were separated on 1% agarose gel (Sigma, USA) mixed with 0.5 µg/ml ethidium bromide (Sigma, USA) along with GeneRuler 1 kb plus DNA ladder.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

What is claimed is:

1. An interfering ribonucleic acid (RNAi) cassette comprising a double-stranded ribonucleic acid (dsRNA) template and a selectable marker both operatively linked to a plant-specific promoter, wherein the dsRNA template comprises SEQ ID NO: 2, and wherein the dsRNA template is adapted to produce RNAi to inhibit synthesis of the polyketide synthase of *Aspergillus* aflatoxin biosynthesis.

2. The RNAi cassette of claim 1, wherein the plant-specific promoter comprises an endosperm promoter or a glycinin promoter.

3. The RNAi cassette of claim 1, wherein the selectable marker comprises a bialaphos resistance (bar) gene.

4. A host comprising an interfering ribonucleic acid (RNAi) cassette, the RNAi cassette comprising a double-stranded ribonucleic acid (dsRNA) template and a selectable marker both operatively linked to a plant-specific promoter, wherein the dsRNA template comprises SEQ ID NO: 2.

5. The host of claim 4, wherein the host is *Agrobacterium*.

6. A transgenic plant engineered to inhibit synthesis of *Aspergillus* aflatoxin, wherein the transgenic plant expresses an interfering ribonucleic acid (RNAi) cassette, the RNAi cassette comprising a double-stranded ribonucleic acid (dsRNA) template and a selectable marker both operatively linked to a plant-specific promoter, wherein the dsRNA template comprises SEQ ID NO: 2, and wherein the dsRNA template is expressed in the transgenic plant thereby producing RNAi adapted to inhibit synthesis of the polyketide synthase.

7. The transgenic plant of claim 6, wherein the plant-specific promoter comprises an endosperm promoter or a glycinin promoter.

8. The transgenic plant of claim 6, wherein the selectable marker comprises a bialaphos resistance (bar) gene.

9. The transgenic plant of claim 6, wherein the plant is a maize species or a peanut species.

* * * * *

SEQUENCE LISTING

```
<160> NUMBER OF SEQ ID NOS: 14

<210> SEQ ID NO 1
<211> LENGTH: 6594
<212> TYPE: DNA
<213> ORGANISM: Aspergillus parasiticus

<400> SEQUENCE: 1
tgcttccatc cagtttcaac aatctcatac cctatcccac aatggctcaa tcaaggcaac      60
tctttctctt cggcgatcag acagcggatt ttgttcccaa gctccgcagt ttactatccg     120
tccaggacag ccctattcta gccgcctttc ttgaccagtc ccactatgtc gtgcgagccc     180
agatgctgca gagcatgaac acggttgatc acaagttggc tcgaaccgct gacctgcgcc     240
aaatggtcca gaagtatgtc gacggcaaac tgacccctgc atttcgaacc gctctagtgt     300
gcctctgcca gttgggatgc ttcatccggg aatatgagga atctggcaac atgtacccac     360
agcccagtga cagctacgtg ctgggattct gcatgggttc cttggccgct gtggcggtaa     420
gctgcagtcg ctccctgtca gagctgctgc ctatcgctgt acaaactgtg ttgattgcct     480
tccgcctcgg tctttgcgcc ctggagatgc gggatcgggt ggatgggtgt agcgatgatc     540
gaggtgaccc ttggtctacc attgtttggg gtctggatcc ccagcaagct cgtgatcaga     600
ttgaagtgtt ctgtcggacc acaaacgtac ctcagacaag gcgtccgtgg atcagctgca     660
tctctaagaa tgccatcacc ctaagtggca gtccatccac tttgagggcg ttctgtgcga     720
tgcctcagat ggcccagcac cggactgccc caattccat ctgtttaccg gcccacaatg     780
gcgccctctt cacgcaggca gatatcacta ccatactaga cacgacgcct accactcctt     840
gggagcaact gcccggccaa ataccttata tttcccatgt cacggggaat gtagtccaga     900
cttccaacta ccgggacctt atagaggtag ccctgtctga gactctcttg gagcaagtgc     960
gactagactt ggttgagact ggactgccac gccttttgca atctcgtcag gtcaagagcg    1020
tcaccatcgt accattcttg actcgcatga atgagacaat gagcaacatt ctcccagaca    1080
```

```
gctttatcag tacagagaca aggactgaca ccggacgagc catcccagct tcaggtcgac    1140
caggcgcagg caagtgcaag ctggctattg tgtccatgtc ggggaggttc cctgaatcac    1200
cgaccaccga aagcttttgg gaccttctat acaaagggtt ggatgtttgt aaagaggttc    1260
cccgtcgacg gtgggacatc aacacgcatg tggatcccag cgggaaagca cgaaacaaag    1320
gggctaccaa atggggctgc tggctagatt tctcaggcga ttttgatccc cgattctttg    1380
ggatctcgcc caaagaggcg ccacagatgg atccagctca gcgcatggcc ttgatgtcta    1440
cttacgaggc aatggagcgg gctggtttgg ttcccgacac cacgccgtcg acccagcgag    1500
accgcattgg ggtcttccac ggagtcacca gtaacgactg gatggagacc aatacagccc    1560
agaacattga cacatacttc atcaccggtg gaaatcgggg gtttattccc gggcgcatta    1620
acttctgttt cgaatttgcc ggacccagct ataccaatga cacggcctgt tcatccagtc    1680
tagctgccat ccacctggcc tgcaattctc tctggcgggg cgactgtgac acggcggtgg    1740
caggaggaac taacatgatc tatactcctg atggtcacac aggattggac aaagggttct    1800 ttcttttcccg gactggcaac tgcaaaccct acgacgacaa ggccgatggt tactgccgag    1860
ctgagggggg cggacggtg ttcatcaaac ggctggaaga tgctctggca gataatgacc    1920
ccatccttgg cgttattcta gatgctaaaa ctaatcactc agccatgtcg gagtcgatga    1980
ctcggccgca cgtgggcgcc caaatcgata acatgacggc ggcgctgaat accactggac    2040
tccatcccaa tgactttagc tacattgaga tgcatggcac tggcacccag gtaggggatg    2100
cggtggagat ggagtcagtc ctgtcggtgt ttgcgccgtc cgaaaccgcc agaaaggcgg    2160
atcagccact atttgtcggc tcagccaagg ccaacgtagg acatggagag ggagtgtctg    2220
gggttacgag ccttattaag gttctgatga tgatgcagca cgataccata cctcctcact    2280
gcggcatcaa accgggcagc aaaatcaacc gcaacttccc tgatcttgga gctcgcaatg    2340
tgcacatcgc ctttgaaccc aagccctggc cacgaacaca cactccgcgc agggtgctta    2400
tcaacaactt cagtgccgcg ggagggaata ctgccttgat agtggaagac gctccggagc    2460
gtcactggcc gacagagaag gatcgcgcgct ctagtcatat cgtcgccctg tctgcgcatg    2520
tgggggcttc catgaaaacc aacctcgaac gactgcatca gtatctcctg aaaaacccccc    2580 acactgatct cgcgcagctg tcatatacta ctactgcgcg tcgatggcat tatctacacc    2640
gagtgagcgt cactggcgcg tctgttgaag aagtgactcg caagctagag atggccatac    2700
agaacgggga cggagtcagt cgacccaaaa gcaagccgaa gattctctttt gctttcacgg    2760 gacaagggtc tcaatatgca actatgggta agcaggtgta cgatgcgtat ccatctttca    2820
gagaggacct ggagaagttt gatcggttgg cgcaaagtca tggcttccct agctttcttc    2880
acgtctgtac ttcacctaaa ggggatgtgg aagagatggc tcccgttgtg gtgcaactgg    2940
ctatcacttg tctccaaatg gcccttacta acctcatgac ctccttcggg atccgtcccg    3000
atgtgacagt ggggcatagt ttgggtgaat ttgcagccct gtatgcggcg ggagttcttt    3060
cggcctcaga cgtcgtttac cttgttggtc aaagagcgga gctactccag gagcgctgcc    3120
aacgcgggac gcatgccatg ctggctgtga aagctacccc tgaagcgttg tcccaatgga    3180
tccaggatca tgactgtgag gtggcctgta ttaatgccc tgaagatacc gttctcagtg    3240
gcaccactaa gaatgttgcc gaggttcaac gcgctatgac ggacaacggg atcaaatgca    3300
cgctgttgaa actgccgttt gccttccatt ctgcccaggt gcaacctatt ctggacgact    3360
ttgaggccct ggctcaggga gcgacatttg ccaagcctca actactaatt ctctctccct    3420
```

```
tgctgcggac agaaatccac gaacaaggcg tcgtgactcc atcatatgtc gcgcaacatt    3480
gtcgtcacac cgtagatatg gcccaagctt tgagatctgc tcgagaaaag ggactcatcg    3540
acgacaaaac cctcgtcatt gagctgggac cgaagccatt aatctcgggc atggtgaaaa    3600
tgacactggg agacaaaatt agcaccttac ccactctagc acctaacaag gccatttggc    3660
ccagcctgca gaagattctc acctcggtct acacgggtgg gtgggatatt aattggaaga    3720
aatatcacgc ccctttcgcc tcctcccaga aggtggtgga tctgccgagc tacggctggg    3780
atttgaagga ctactacatc ccgtatcagg gtgactggtg tctgcatcgc caccagcagg    3840
attgtaagtg cgccgctcct ggccacgaaa tcaaaacggc cgactaccaa gtgcctcctg    3900
agtcgacgcc tcaccgtcca tccaagctgg accctagcaa ggaggccttc cccgaaatca    3960
agaccaccac gacactccat cgagtggtgg aagagacgac caaacctttg ggcgccaccc    4020
tagttgtgga gacagacata tctcggaagg atgtcaacgg cctcgtcga gggcaccttg    4080 tcgatgggat cccttttgtgt accccttcct tttatgctga catcgccatg caagtgggcc    4140
aatacagtat gcaacggctc cgtgcgggac atccgggggc cggtgccata gatggccttg    4200
tggacgtgtc cgacatggtg gtggacaaag cgttggttcc ccatgggaag ggacctcaat    4260
tgctgcgcac gacgcttacc atggagtggc cgcccaaggc tgctgctact acgcgaagcg    4320
ccaaagtcaa attcgccacc tattttgccg atgggaagct cgatacggag catgccagct    4380
gtactgtcag attcacaagc gatgcacagt tgaaatctct acgccggtct gtgtccgagt    4440
acaagaccca cattcgtcag ttacatgatg gccatgctaa gggacagttc atgcgataca    4500
ataggaagac cgggtacaag ctcatgagca gcatggctcg gtttaatccc gactacatgc    4560
tcctagatta tctggtgctg aacgaagcag agaacgaggc agcaagtggt gtagacttct    4620
cgttgggatc gtcggaaggc accttcgcag ctcacccagc tcacgtcgat gccatcactc    4680
aggtggccgg cttctgctatg aatgccaatg acaatgtcga cattgagaaa caggtctacg    4740
ttaatcacgg ttgggactcg ttccagatct accaaccgct ggataatagc aagtcttacc    4800
aggtctacac caagatgggt caagcgaagg agaatgattt ggtgcatggc gatgtggtag    4860
ttctggacgg agaacaaatc gttgctttct tccgcggcct tacgctgcga tcagttcctc    4920
gtggtgcact gcgtgtcgtc ctgcagacta cagtgaaaaa ggccgatcgc caactaggat    4980
ttaagacaat gccgtcgccg ccgcccccga caacgacaat gccaatatcg ccttataaac    5040
cagctaatac tcaggtttcc agccaagcta ttccagcaga ggccactcat tctcacaccc    5100
cgccacagcc aaaagcattcc ccggtaccgg aaactgccgg aagcgctcca gcggcaaaag    5160
gagtaggtgt cagtaacgaa aagttagatg ctgtaatgcg agtcgtttcg gaggagagtg    5220
gaattgccct cgaggagctc accgatgaca gcaactttgc tgacatgggc atcgactctc    5280
tgagttcaat ggtcattggg agccgcttca gagaggacct ggggctggac ctggggcctg    5340
agttttctct tttcattgac tgcactaccg tgcgtgcctt gaaagacttc atgttgggaa    5400
gcggggatgc tggcagtggc tccaatgtag aagatcctcc cccatcagct actcccggca    5460
tcaaccccga aaccgattgg tctagcagtg cctctgatag tattttcgcc agcgaagacc    5520
acggtcattc gagtgagtcc ggcgccgaca ccggaagtcc gcctgcactt gatctgaagc    5580
cctactgccg cccctcaact tctgtcgtcc tacaaggtct acctatggtg gcgcggaaaa    5640
ctctgtttat gctccctgat ggcgggggggt ctgcgttctc ctacgcctcc ctgccgcgcc    5700
tcaaatcaga tactgccgtt gtgggcctga attgccctta tgctcgggat cccgagaaca    5760
tgaactgcac acatggagct atgattgaga gcttttgcaa tgagatccgg cggcgacagc    5820
```

| | | | |
|---|---|---|---|
| cacggggccc | ctatcacctg | ggcggctggt | cgtccggtgg tgcattcgct tacgtcgtgg | 5880 |
| ccgaggcact | tgttaaccaa | ggcgaggagg | tgcattcgtt aatcatcatt gatgcgccta | 5940 |
| ttccccaagc | catggaacaa | cttccccgag | cattttacga gcactgcaat agcattggat | 6000 |
| tgttcgctac | ccagccgggg | gctagtccgg | acggctcgac tgagcctcca tcctacttaa | 6060 |
| tcccacactt | taccgctgtg | gtggatgtga | tgctggatta caagctggcc ccgttgcatg | 6120 |
| cgcgccggat | gcccaaggtc | ggcatcgtct | gggcggcaga tacagtcatg gacgagcggg | 6180 |
| acgctcccaa | gatgaaagga | atgcatttta | tgattcagaa gcggacggaa tttggtcccg | 6240 |
| atgggtggga | tacgatcatg | cccggggcct | cgtttgacat tgtccgagca gacggtgcta | 6300 |
| atcattttac | gttgatgcaa | aaggaacatg | tctctataat tagcgatctg atcgaccggg | 6360 |
| tcatggctta | gcaaaccccg | ttttggtggg | ccgcccgcat acttacaact attatggctc | 6420 |
| ctggcggagg | gaggaagcaa | gggcgtgttt | ttcagttgtt gccgctgtta gaaatgacga | 6480 |
| aactgtggtt | tacaaacttg | ttttacaggg | ctcattctgt atattgattc caattccata | 6540 |
| aataggtatt | ttaacgatga | tagcatatcc | accattttag acaattagtc tccc | 6594 |

<210> SEQ ID NO 2
<211> LENGTH: 624
<212> TYPE: DNA
<213> ORGANISM: Artificial Sequence
<220> FEATURE:
<223> OTHER INFORMATION: Sequence for RNAi vector

<400> SEQUENCE: 2

| | | | |
|---|---|---|---|
| tctagactcg | agtatgcggc | gggagttctt | tcggcctcag acgtcgttta ccttgttggt | 60 |
| caaagagcgg | agctactcca | ggagcgctgc | caacgcggga cgcatgccat gctggctgtg | 120 |
| aaagctaccc | ctgaagcgtt | gtcccaatgg | atccaggatc atgactgtga ggtggcctgt | 180 |
| attaatggcc | ctgaagatac | cgttctcagt | ggcaagaccc acattcgtca gttacatgat | 240 |
| ggccatgcta | agggacagtt | catgcgatac | aataggaaga ccgggtacaa gctcatgagc | 300 |
| agcatggctc | ggtttaatcc | cgactacatg | ctcctagatt atctggtgct gaacgaagca | 360 |
| gagaacgagg | cagcaagtgg | tgtagacttc | tcgttgggat cgtcggaagg catccccaag | 420 |
| ccatggaaca | acttccccga | gcattttacg | agcactgcaa tagcattgga ttgttcgcta | 480 |
| cccagccggg | ggctagtccg | gacggctcga | ctgagcctcc atcctactta atcccacact | 540 |
| ttaccgctgt | ggtggatgtg | atgctggatt | acaagctggc cccgttgcat gcgcgccgga | 600 |
| tgcccaaggt | cgactagtaa | gctt | | 624 |

<210> SEQ ID NO 3
<211> LENGTH: 203
<212> TYPE: DNA
<213> ORGANISM: Artificial Sequence
<220> FEATURE:
<223> OTHER INFORMATION: Sequence for RNAi construct

<400> SEQUENCE: 3

| | | | |
|---|---|---|---|
| gtatgcggcg | ggagttcttt | cggcctcaga | cgtcgtttac cttgttggtc aaagagcgga | 60 |
| gctactccag | gagcgctgcc | aacgcgggac | gcatgccatg ctggctgtga aagctacccc | 120 |
| tgaagcgttg | tcccaatgga | tccaggatca | tgactgtgag gtggcctgta ttaatggccc | 180 |
| tgaagatacc | gttctcagtg | gca | | 203 |

<210> SEQ ID NO 4

```
<211> LENGTH: 198
<212> TYPE: DNA
<213> ORGANISM: Artificial Sequence
<220> FEATURE:
<223> OTHER INFORMATION: Sequence for RNAi construct

<400> SEQUENCE: 4
agacccacat tcgtcagtta catgatggcc atgctaaggg acagttcatg cgatacaata    60
ggaagaccgg gtacaagctc atgagcagca tggctcggtt taatcccgac tacatgctcc   120
tagattatct ggtgctgaac gaagcagaga acgaggcagc aagtggtgta gacttctcgt   180
tgggatcgtc ggaaggca                                                 198

<210> SEQ ID NO 5
<211> LENGTH: 200
<212> TYPE: DNA
<213> ORGANISM: Artificial Sequence
<220> FEATURE:
<223> OTHER INFORMATION: Sequence for RNAi construct

<400> SEQUENCE: 5
tccccaagcc atgaacaac ttccccgagc attttacgag cactgcaata gcattggatt     60
gttcgctacc cagccggggg ctagtccgga cggctcgact gagcctccat cctacttaat   120
cccacacttt accgctgtgg tggatgtgat gctggattac aagctggccc cgttgcatgc   180
gcgccggatg cccaaggtcg                                               200

<210> SEQ ID NO 6
<211> LENGTH: 203
<212> TYPE: DNA
<213> ORGANISM: Artificial Sequence
<220> FEATURE:
<223> OTHER INFORMATION: Sequence for RNAi construct

<400> SEQUENCE: 6
gtaagcggcg ggacttcttt cggcctcagc cgtcgtttac cttcttggtc aaagagcggc    60
gctactccag gagcgctccc aacgcgggac gcttgccatg ctgggtgtga agctaccccc   120
ggaagcgttg tctcaatgga tccaggatga tgactgtgag ctggcctgaa ttaattgccc   180
tgaagagacc gttctcactg gca                                           203

<210> SEQ ID NO 7
<211> LENGTH: 203
<212> TYPE: DNA
<213> ORGANISM: Artificial Sequence
<220> FEATURE:
<223> OTHER INFORMATION: Sequence for RNAi construct

<400> SEQUENCE: 7
gtatccggcg ggagttcttt cggccacaga cgtcggttac cttgttggtc aaagagcgga    60
gctactccag gagcgctgcc aacgcgggtc gcatgcaatg ctggctgtga agctaccccc   120
tgaagggttc tcccaatgga tccaggatca tgactgtggg gtggcctgta ttaaaggccc   180
tgaagatacc gttctcagtg gca                                           203

<210> SEQ ID NO 8
<211> LENGTH: 203
<212> TYPE: DNA
<213> ORGANISM: Artificial Sequence
<220> FEATURE:
<223> OTHER INFORMATION: Sequence for RNAi construct

<400> SEQUENCE: 8
```

```
gaatgcggcg ggagttctttt cggcctcaga cgtcgtttac cttgttggtc aaacagcgga      60
gctactccag gagcgctgcc aacgcgggac gcatgccatg ctggctgtga agctacccc      120 tgaagcgttg tcccaatgga tccaggatca tgactgtgag gtggcctgta ttaatggccc     180
tgaagatacc gttctcagtg gca                                            203
```

```
<210> SEQ ID NO 9
<211> LENGTH: 23
<212> TYPE: DNA
<213> ORGANISM: Artificial Sequence
<220> FEATURE:
<223> OTHER INFORMATION: Primer

<400> SEQUENCE: 9
gatcccatca agcttatcga tac                                             23

<210> SEQ ID NO 10
<211> LENGTH: 21
<212> TYPE: DNA
<213> ORGANISM: Artificial Sequence
<220> FEATURE:
<223> OTHER INFORMATION: Primer

<400> SEQUENCE: 10
ccaaatgttt gaacgatcgg g                                               21

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
gtagctttga cagccagcat                                                 20

<210> SEQ ID NO 12
<211> LENGTH: 21
<212> TYPE: DNA
<213> ORGANISM: Artificial Sequence
<220> FEATURE:
<223> OTHER INFORMATION: Primer

<400> SEQUENCE: 12
ccaaatgttt gaacgatcgg g                                               21

<210> SEQ ID NO 13
<211> LENGTH: 21
<212> TYPE: DNA
<213> ORGANISM: Artificial Sequence
<220> FEATURE:
<223> OTHER INFORMATION: Primer

<400> SEQUENCE: 13
tgtggatgtc tcggttgttg a                                               21

<210> SEQ ID NO 14
<211> LENGTH: 21
<212> TYPE: DNA
<213> ORGANISM: Artificial Sequence
```

-continued

```
<220> FEATURE:
<223> OTHER INFORMATION: Primer

<400> SEQUENCE: 14
cttgaacatg tggcggatca g                                    21
```